United States Patent
Duffey

(10) Patent No.: US 10,228,322 B2
(45) Date of Patent: Mar. 12, 2019

(54) APPARATUS FOR AND METHOD OF SENSING FLUORINE CONCENTRATION

(71) Applicant: Cymer, LLC, San Diego, CA (US)

(72) Inventor: Thomas Patrick Duffey, San Diego, CA (US)

(73) Assignee: CYMER LLC, San Diego, CA (US)

(*) Notice: Subject to any disclaimer, the term of this patent is extended or adjusted under 35 U.S.C. 154(b) by 0 days.

(21) Appl. No.: 15/648,845

(22) Filed: Jul. 13, 2017

(65) Prior Publication Data
US 2019/0017924 A1    Jan. 17, 2019

(51) Int. Cl.
*G01N 21/00* (2006.01)
*G01N 21/17* (2006.01)
*G01N 29/24* (2006.01)
*G01N 21/31* (2006.01)

(52) U.S. Cl.
CPC ..... *G01N 21/1702* (2013.01); *G01N 21/3151* (2013.01); *G01N 29/2425* (2013.01); *G01N 2021/1704* (2013.01); *G01N 2021/1708* (2013.01)

(58) Field of Classification Search
CPC ................ G01N 21/3151; G01N 29/2425
USPC .................................................. 356/435–440
See application file for complete search history.

(56) References Cited

U.S. PATENT DOCUMENTS

| | | | | |
|---|---|---|---|---|
| 4,535,241 A | * | 8/1985 | Eberhardt | G01N 21/39 250/338.5 |
| 6,240,117 B1 | * | 5/2001 | Gong | G03F 7/70558 372/57 |
| 2002/0051132 A1 | * | 5/2002 | Ohno | G01N 33/0052 356/437 |
| 2005/0117155 A1 | * | 6/2005 | Kosterev | G01N 21/1702 356/432 |
| 2011/0214481 A1 | * | 9/2011 | Kachanov | G01N 21/1702 73/24.02 |
| 2012/0151994 A1 | * | 6/2012 | Hung | G01N 21/1702 73/24.02 |
| 2013/0044314 A1 | * | 2/2013 | Koulikov | G01N 21/1702 356/72 |
| 2013/0239658 A1 | * | 9/2013 | Lust | G01N 21/17 73/24.02 |

* cited by examiner

*Primary Examiner* — Isiaka Akanbi
(74) *Attorney, Agent, or Firm* — Arent Fox LLP

(57) ABSTRACT

Disclosed is an apparatus for and method of measuring the concentration of F2 in the laser gas used in an excimer laser. Quartz Enhanced Photoacoustic Spectroscopy is used to obtain a direct measurement of F2 concentration quickly and using only a small sample volume.

1 Claim, 4 Drawing Sheets

APPARATUS FOR AND METHOD OF SENSING FLUORINE CONCENTRATION

FIELD

The present disclosure relates to excimer lasers and in particular to equipment for and methods of monitoring the composition of laser gas in excimer lasers.

BACKGROUND

Excimer lasers are well known. One important use of excimer lasers is as a light source for integrated circuit lithography. One type of excimer laser currently being supplied in substantial numbers for integrated circuit lithography is the ArF laser which produces ultraviolet light at a wavelength of 193 nm. A similar excimer laser, the KrF laser, provides ultraviolet light at 248 nm. Both of these wavelengths are considered to reside in the deep ultraviolet ("DUV") portion of the electromagnetic spectrum.

These lasers typically operate in a pulse mode. The laser beam is produced in a laser chamber containing a gain medium created by a discharge through a laser gas between two electrodes. For an ArF laser the laser gas is typically about 3 to 4% argon, 0.1% fluorine and 96 to 97% neon. For a KrF laser, the laser gas is typically about 1% krypton, 0.1% fluorine and about 99% neon.

Fluorine is the most reactive element, and it becomes even more reactive when ionized during an electric discharge. Special care must be exercised to utilize in these laser chambers materials such as nickel-coated aluminum which are reasonably compatible with fluorine. Further, laser chambers may be pretreated with fluorine to create passivation layers on the inside of the laser chamber walls. However, even with this special care, fluorine will react with the walls and other laser components producing metal fluoride contaminants and resulting in a relatively regular depletion of fluorine gas. The rates of depletion are dependent on many factors, but for a given laser at a particular time in its useful life, the rates of depletion depend primarily on the pulse rate and load factor if the laser is operating. If the laser is not operating, the depletion rate is substantially reduced. The rate of depletion is further reduced if the gas is not being circulated. To make up for this depletion, new fluorine or a gas mixture containing fluorine is typically injected at regular intervals. These and other details of the operation of these lasers can be found in U.S. Pat. No. 6,240,117, titled "Fluorine Control System with Fluorine Monitor" issued May 29, 2001, the entire disclosure of which is hereby incorporated by reference.

In some present systems, indirect measures of laser performance are used to estimate F2 consumption. Such indirect measures are generally effective to provide long term reliable operation of these excimer lasers in a manufacturing environment. However, various factors (changing operating point, contaminant generation) can lead to errors in the estimate, causing drift in performance over gas life and ultimately unacceptable error rates.

Direct measurement of F2 concentration in the gas would avoid these difficulties. Direct F2 measurement is possible with chemical sensors but these are typically slow and require large sample volumes (or continuous flow) of gas to establish an accurate reading. Sampling significant fractions of the gas in the chamber would increase overall consumption of gas and likely lead to changes in performance while sampling is taking place (i.e., the chamber pressure drops considerably when a F2 measurement is made). Additionally, frequent and time-consuming calibration is necessary.

There is therefore a need for an apparatus for and method of determining fluorine depletion in fluorine-based excimer lasers such as ArF and KrF excimer lasers. This need is especially acute in lasers having a dual chamber design and pulsed power architecture where the two chambers receive identical charge voltages thus rendering estimation of fluorine consumption more difficult.

SUMMARY

The following presents a simplified summary of one or more embodiments in order to provide a basic understanding of the embodiments. This summary is not an extensive overview of all contemplated embodiments and is not intended to identify key or critical elements of all embodiments nor set limits on the scope of any or all embodiments. Its sole purpose is to present some concepts of one or more embodiments in a simplified form as a prelude to the more detailed description that is presented later.

According to one aspect there is disclosed an apparatus comprising a laser chamber adapted to retain a laser gas containing fluorine, a gas cell in selective fluid communication with the laser chamber for retaining a sample of the laser gas, a radiation source arranged to irradiate at least a portion of the gas sample with radiation modulated at a reference frequency to produce acoustic waves in the gas sample, a transducer located in the gas cell and having a resonant frequency substantially the same as the reference frequency and subjected to the acoustic waves in such a manner as to cause at least a portion of the transducer to vibrate for generating an electrical signal indicative of a frequency at which the transducer vibrates, and a circuit arranged to receive the electrical signal and for generating an output signal indicative of a magnitude of a frequency component of the electrical signal at the reference frequency. The radiation source may be a laser which may be a pulsed laser or an externally modulated continuous wave laser. The radiation source may be an LED. The transducer may comprise a piezoelectric quartz tuning fork. The apparatus may also include an acoustic resonator located in the gas cell and acoustically coupled to the transducer arranged to amplify the acoustic waves. The apparatus may also include a preamplification circuit. The circuit may comprise a lock-in amplifier. The radiation source may comprise a laser having a wavelength between about 180 nm and about 410 nm or having a wavelength between about 360 nm and about 397 nm. The radiation source may comprise continuous wave laser having a wavelength between about 360 nm and about 375 nm. The apparatus may also include a laser controller arranged to receive the electrical signal and adapted to determine based at least in part on the electrical signal a concentration of F2 in the sample gas. The apparatus may also include a gas supply system responsively connected to the laser controller and adapted to supply gas containing F2 to the laser chamber based at least in part on the concentration of F2 in the sample gas as determined by the laser controller.

According to another aspect there is disclosed an apparatus comprising a laser chamber adapted to retain a laser gas containing fluorine, a gas cell in selective fluid communication with the laser chamber for retaining a sample of the laser gas, a frequency generator for producing a frequency signal having a reference frequency, a radiation arranged to receive the frequency signal and to irradiate at least a portion of the gas sample with radiation modulated at the reference frequency to produce acoustic waves in the gas sample, an acoustic resonator located in the gas cell and arranged to amplify the acoustic waves, a piezoelectric quartz tuning fork located in the gas cell and having a resonant frequency substantially the same as the reference frequency and subjected to the acoustic waves in such a manner as to cause at least a portion of the piezoelectric quartz tuning fork to vibrate for generating an electrical signal indicative of a frequency at which the piezoelectric quartz tuning fork vibrates, a preamplification circuit arranged to receive the electrical signal to produce an amplified electrical signal, a lock-in amplifier arranged to receive the amplified electrical signal and for generating an output signal indicative of a magnitude of a frequency component of the electrical signal at the reference frequency, a laser controller arranged to receive the electrical signal and adapted to determine based at least in part on the electrical signal a concentration of F2 in the sample gas and to generate an indication that it is necessary to add gas containing F2 to the laser chamber, and a gas supply system responsively connected to the laser controller and adapted to supply gas containing F2 to the laser chamber based at least in part on the indication from the laser controller.

According to another aspect there is disclosed a method comprising the steps of adding a sample of laser gas from a laser chamber to a gas cell, irradiating at least a portion of the gas sample with radiation modulated at a reference frequency to produce acoustic waves in the gas sample, the acoustic waves inducing vibrations in a transducer located in the gas cell and having a resonant frequency substantially the same as the reference frequency, the transducer generating an electrical signal indicative of the vibrations, and generating based on the electrical signal an output signal indicative of a magnitude of a frequency component of the electrical signal at the reference frequency. The irradiating step may be performed using a laser or an LED. The method may further comprise the step of determining based at least in part on the electrical signal a concentration of F2 in the sample of laser gas and generating an indication that it is necessary to add gas containing F2 to the laser chamber. The method may further comprise the step of supplying gas containing F2 to the laser chamber based at least in part on the indication.

DETAILED DESCRIPTION

Figure 1A:
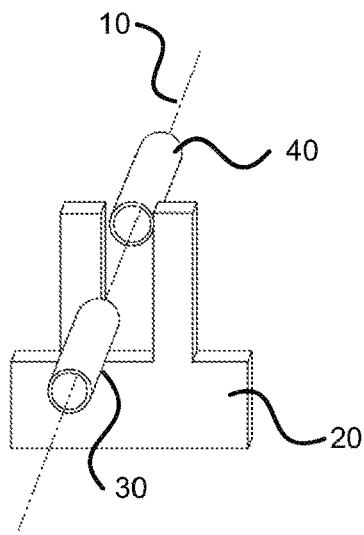
FIGS. 1A-1D are diagrams showing various alternative configurations for a Quartz Enhanced Photoacoustic Spectroscopy detector.

Various embodiments are now described with reference to the drawings, wherein like reference numerals are used to refer to like elements throughout. In the following description, for purposes of explanation, numerous specific details are set forth in order to promote a thorough understanding of one or more embodiments. It may be evident in some or all instances, however, that any embodiment described below can be practiced without adopting the specific design details described below. In other instances, well-known structures and devices are shown in block diagram form in order to facilitate description of one or more embodiments.

According to one aspect, disclosed is the use of a spectroscopic technique - - - Quartz Enhanced Photoacoustic Spectroscopy, or QEPAS - - - to measure the fluorine number density in the gas. QEPAS for this purpose involves absorption of a beam of light by a sample of fluorine-containing gas producing a (small) temperature change in the gas through which the light passes. Modulating the intensity or frequency of the light produces a modulation in temperature. This modulated temperature in turn produces a modulation in pressure and density, i.e. an acoustic wave, in the gas. The acoustic wave is detected using a small quartz tuning fork resonant with the modulation frequency. The fork and beam are situated such that the acoustic wave produces an anti-symmetric displacement of the fork tines, generating an electrical signal through the piezoelectric effect in the quartz. In other words, the acoustic resonator and the beam are positioned relative to one another in such a way that the beam generates acoustic waves that move the tuning fork tines in different directions (e.g., in opposition) to generate a piezoelectric signal. This signal is amplified and its magnitude measured accurately using phase-sensitive detection of the signal component at the modulation frequency. A detailed review of the basic QEPAS technique can be found in Kosterev et al., Applications of Quartz Tuning Forks in Spectroscopic Gas Sensing, *Review of Scientific Instruments* No. 76, 0439105:1-043105:9 (2005). Using this technique it is possible to produce a stable reading within a few seconds using less than one cubic centimeter of sample volume.

Figure 1B:
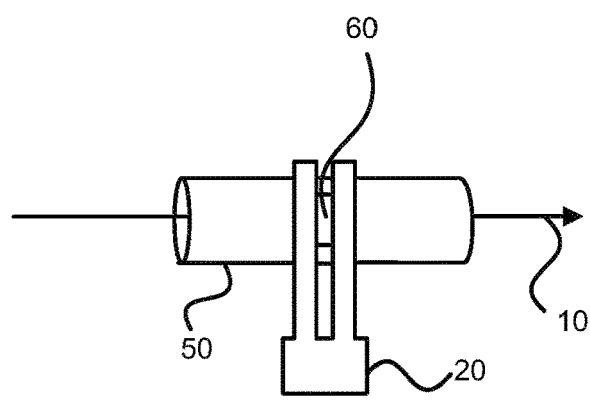
Figure 1C:
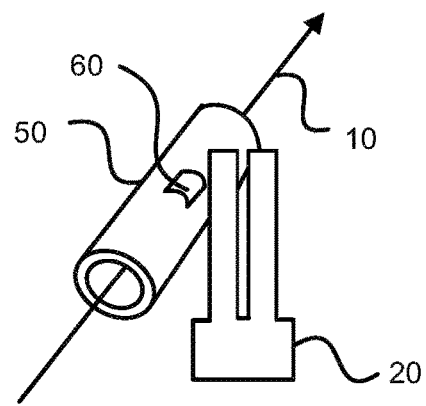
Figure 1D:
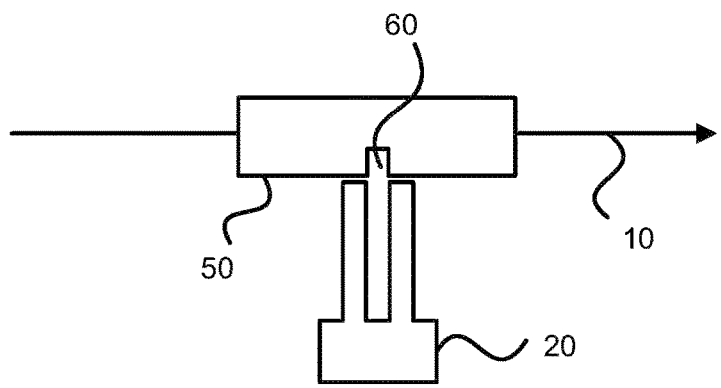

There are two major approaches to using this technique. In the first, shown in FIG. 1A, a beam 10 from a high beam-quality laser is typically focused between the tines of a quartz tuning fork 20. Often small tubes 30 and 40 placed respectively on either side of the fork and through which the beam 10 passes are used as an acoustic resonator to increase the magnitude of the acoustic signal. In the second technique, used in conjunction with a lower beam quality laser used as a light source, e.g. light from an LED, the beam 10 is focused through a larger tube 50 as shown in FIG. 1B that runs parallel to the plane of the tines of the tuning fork 20. A small slit 60 in the tube 50 located near the space between the tines of the fork 20 emits the acoustic wave into a region between the tines. This version is termed "off-beam QEPAS." Other possible arrangements for off-beam QEPAS are shown in FIGS. 1C and 1D. Additional information is available in Liu et al., Trace gas detection based on off-beam quartz enhanced photoacoustic spectroscopy: Optimization and performance evaluation. *Review of Scientific Instruments* 81, No. 10 (2010): 103103. Additional information is also available in U.S. Pat. No. 7,245,380, issued Jul. 17, 2007 and titled "Quartz Enhanced Photoacoustic Spectroscopy", the specification of which is incorporated by reference.

For F2, the broad continuous absorption band that occurs between 210 and 500 nm, peaking at 285 nm, can be used. For typical concentration of F2 in excimer laser gas, the absorption at the peak wavelength of 285 nm, will typically be about $7 \times 10^{-4}$/cm. This absorption is quite weak, but the QEPAS technique has successfully been used to measure species where the absorption coefficient was orders of magnitude lower. To measure at this level, 1.2 W of optical power was required at 762 nm. Such high powers are not readily available in the UV portion of the spectrum, but to ensure good signal the light source should be chosen to optimize the product of optical power and absorption coefficient at the light source wavelength.

Any of a number of diode pumped solid state lasers, diode lasers, and LED light sources are available commercially to excite absorption in this wavelength range. For example, suitable lasers for conventional QEPAS are available from Opto Engine LLC in Midvale Utah and/or Changchun New Industries Optoelectronics Technology Co., Ltd. in Changchun PRC as shown in the following table:

| CW 360 nm Laser | 360 nm UV CW laser Near TEM00 beam Power output 1~200 mW single longitudinal mode and low noise versions available | UV-FN-360/1~103 mW UV-FN-360-PL/100-200 mW MLL-FN-360/1~30 mW MSL-FN-360/1~20 mW MSL-FN-360-S/1~20 mW |
| --- | --- | --- |
| CW 375 nm Laser | 375 nm UV CW laser Near TEM00 beam diode laser Power output 1~150 mW | MDL-III-375L/1~50 mW MDL-III-375L/1~150 mW |
| CW low noise 375 nm Laser | 375 nm UV CW laser Near TEM00 beam Low noise diode laser Power output 1~150 mW | MLL-III-375L/1~50 mW MLL-III-375/1~150 mW |
| CW 395 nm Laser | 395 nm UV CW laser Near TEM00 beam diode laser Power output 1~100 mW | MDL-III-395/1~100 mW |
| CW low noise 395 nm Laser | 395 nm UV CW laser Near TEM00 beam Low noise diode laser Power output 1~100 mW | MLL-III-395/1~100 mW |
| CW 397 nm Laser | 397 nm UV CW laser Near TEM00 beam diode laser Power output 1~100 mW | MDL-III-397/1~100 mW |
| CW low noise 397 nm Laser | 397 nm UV CW laser Near TEM00 beam Low noise diode laser Power output 1~100 mW | MLL-III-397/1~100 mW |

It is preferred to use radiation having a wavelength in the range of about 180 nm to about 410 nm and more preferably in the range of about 360 nm to about 397 nm and even more preferably in the range of about 360 nm to about 375 nm. It is also preferred to use a continuous wave (CW) laser. Thus it is presently preferred to use a CW laser having a wavelength between about 360 nm to about 397 nm, more preferably between about 360 nm to about 375 nm, with a power in the range of about 1 mw to about 200 mw or above, and more preferably in the range of about 150 mw to above 200 mw.

Suitable high-power LED diode lasers for use in off-beam QEPAS are available, for example, from Thorlabs, Inc. in Newton, N.J. as shown in the following table:

| Item # | Color | Nominal Wavelength | Minimum LED Power Outputs |
| --- | --- | --- | --- |
| M265L3 | Deep UV | 265 nm | 10 mW |
| M280L3 | Deep UV | 280 nm | 25 mW |
| M30014 | Deep UV | 300 nm | 40 mW |
| M340L4 | Deep UV | 340 nm | 53 mW |
| M365L2 | UV | 365 nm | 190 mW |
| M365P1 | UV | 365 nm | 1150 mW |
| M375L3 | UV | 375 nm | 387 mW |
| M385L2 | UV | 385 nm | 270 mW |
| M385LP1 | UV | 385 nm | 1650 mW |
| M395L4 | UV | 395 nm | 400 mW |
| M405L3 | UV | 405 nm | 870 mW |
| M405LP1 | UV | 405 nm | 1500 mW |
| M42013c | Violet | 420 nm | 750 mW |
| M450LP1 | Royal Blue | 450 nm | 1850 mW |
| M455L3 | Royal Blue | 455 nm | 900 mW |
| M470L3 | Blue | 470 nm | 650 mW |

From this list, for example, Item# M365P1 (wavelength 365 nm, power 1150 mW) would be a good selection because it provides the best combination of power and WL near the peak of absorption.

To summarize, the radiation source may include a continuous wave laser having a wavelength between about 360 nm and about 397 nm. The radiation source may also be a high-power LED. Also, the radiation source intensity or wavelength must have the capability to be modulated at the resonant frequency of the tuning fork. For example, if a laser is used, the laser itself may be a pulsed laser that emits modulated radiation or a continuous wave laser can be modulated by some external method, e.g. use of a chopper wheel or an acousto-optic modulator. In either instance, as used herein, the radiation is modulated. Finally, wavelengths down to 200 nm or below would also work if compact versions of such sources are available.

The excimer laser apparatus into which the senor is incorporated may further include a laser controller arranged to receive the electrical signal and adapted to determine based at least in part on the electrical signal a concentration of F2 in the sample gas. The laser controller may then use the measured F2 concentration to take some action such as supplying F2-containing gas to the laser chamber from which the sample was obtained.

Efficiency can be expected to be adequate because the upper state for the transition under consideration is repulsive; that is, the F2 molecule decays into two F atoms with strong repulsion between them. Hence the absorbed photon energy is mostly converted into kinetic energy of the two atoms. Thermalization of this energy into the gas as a whole should proceed rapidly at densities typical of chamber gas mixes.

Figure 2:
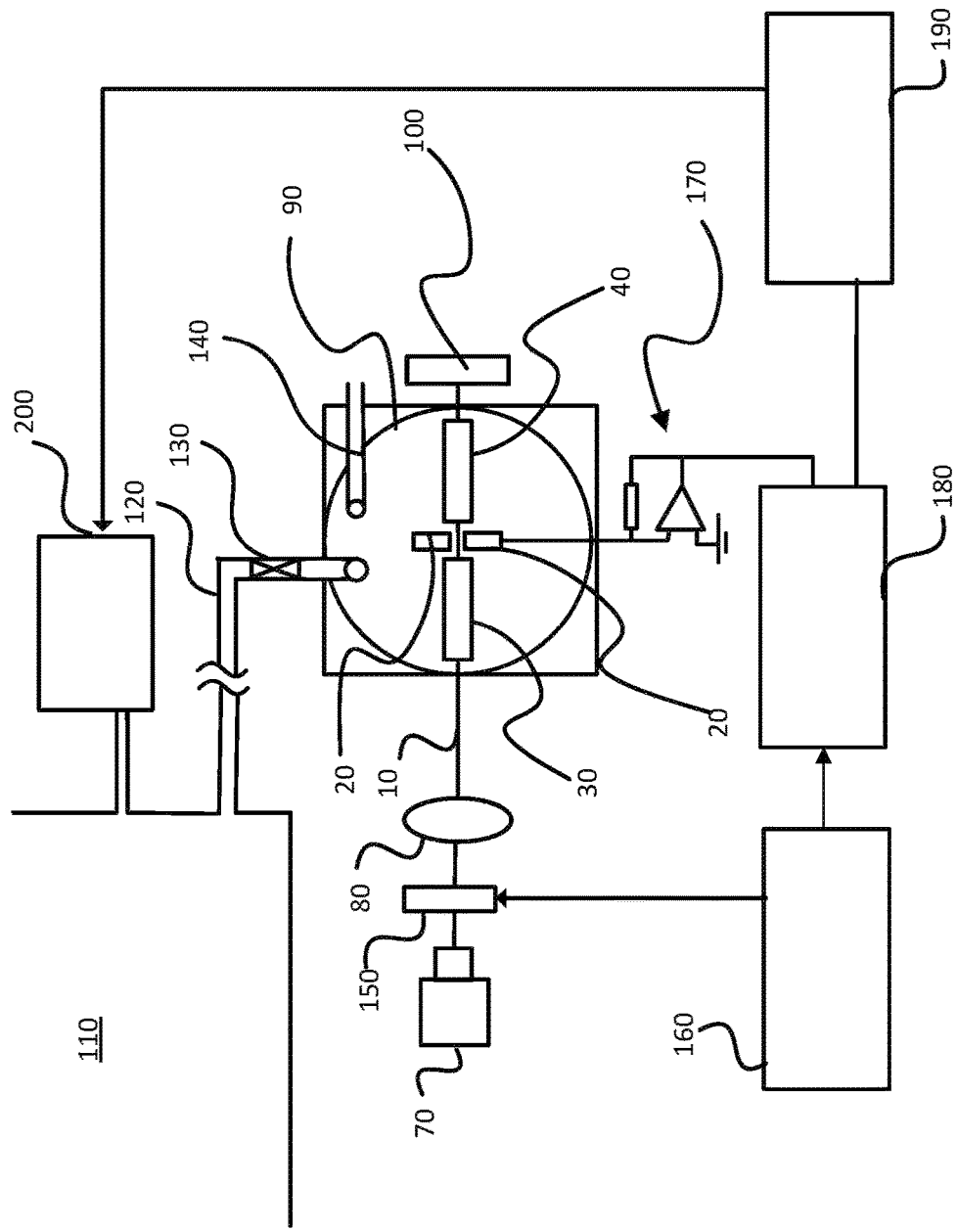
FIG. 2 is a schematic, not-to-scale view of an overall broad conception for a system for supplying gas to a laser chamber based on a measured number concentration of F2 in a laser gas.

FIG. 2 is a schematic view of an system according to one aspect of an embodiment of the present invention. As shown, an F2 sensor includes a light source 70. As described above this light source 70 may be implemented as, for example a laser or an LED. If the light source is a CW laser then its output may be modulated by modulator 150. The light beam 10 from light source 70 is focused by a lens 80 into a gas cell 90. The gas cell 90 contains a piezoelectric quartz tuning fork 20 and small tubes 30 and 40 that act as an acoustic microresonator. Light not absorbed by the gas in the gas cell 90 passes out of the gas cell 90 and into a beam dump 100 thermally isolated from the gas cell 90. Gas is introduced into the gas cell 90 from a laser chamber 110 through a gas inlet 120 containing a valve 130. Gas is vented from the gas cell 90 through a gas outlet 140.

The light source 70 intensity is modulated at a reference frequency by a frequency modulator 150 under the control of a frequency generator 160. The reference frequency corresponds to the resonant frequency of the piezoelectric quartz tuning fork 20. For F2 sensing, intensity modulation is preferred because the absorption band is too wide to permit frequency modulation to be preferred. The piezoelectric quartz tuning fork 20, responding to the acoustic wave, acts as a current source. A transimpedance preamplifier 170 converts the current from the piezoelectric quartz tuning fork 20 into a preamp signal. The preamp signal from the transimpedance preamplifier 170 is routed to a lock-in amplifier 180. The lock-in amplifier 180 outputs a signal proportional to the portion of the preamp signal that is phase-coherent with the modulation (reference) frequency supplied by the frequency generator 160. The output of the lock-in amplifier 180, which is proportional to the F2 number density in the gas sample, is routed to a laser controller 190 in the laser control system. The laser controller 190 uses the information on the F2 number density to determine, for example, when it is necessary to add gas containing F2 to the laser chamber 110. When the laser controller 190 determines that it is necessary to add gas containing F2 to the laser chamber 110 the laser controller 190 generates a control signal that controls a gas supply 200 to supply gas containing F2 to the laser chamber 110 in the manner described below.

There are multiple possible arrangements for integrating the gas cell 90 into the laser gas system. Separate inlet and outlet ports as in the example above are not necessary. Also, in lasers with a multiple chamber configuration such as a chamber for the master oscillator (MO chamber) and a chamber for the power ring amplifier (PRA chamber), separate sensors for each chamber can be used. It is also possible to use a single sensor connected to a port in fluid communication with both chambers such as the gas box manifold. This would allow sampling of either of the MO and PRA chambers, and readily allow isolation of the cell volume from the laser gas to minimize risk of components in the cell contaminating the laser gas as well as allowing the gas cell to be evacuated or back-filled with inert gas or a combination of inert gases between measurements. In addition, connection to the manifold facilitates calibration of the sensor.

In lasers used for semiconductor photolithography, to allow flexibility in F2 concentration, the gas mix in the chamber is typically obtained by mixing gas from two supplies, one that supplies purely inert gases (Ne, Ar or Kr, and sometimes Xe) and another which contains the same inert gases plus F2 at a concentration (typically 1%) much higher that the desired concentration in the chamber. By choosing different proportions of these gas supplies, it is possible to "tune" the F2 concentration to a target value, e.g., about 0.15%, about 0.5%, about 2%, but preferably in the range of between about 0% and about 1%. In a typical application, the ratio of the supplies is about 10:1 to achieve about 0.1% F2. The pure-inert supply is referred to as "bimix" while the F2-bearing supply is referred to as "trimix". In other words, a supplied gas containing no F2 but instead a combination of inert gases such as, for example, Ar and Ne is a "bimix." The Ar concentration could be, for example, about 10% or about 5% or about 1% but preferably in the range of about 3% to about 4% with the balance being another inert gas such as Ne. The gas cell could be filled alternately with bimix and new laser gas mix at each refill to establish 0 ppm and 1000 ppm signal levels.

Thus the system described above permits direct measurement of F2 concentration in laser gas rather than measurement inferred from laser characteristics. The use of the QEPAS apparatus to measure F2 gives a high signal-to-noise ratio and high noise rejection. The high noise rejection is due to the fact that the tuning fork resonance is very sharp ("high Q") and because the tuning fork generates a piezoelectric signal only for oppositional movements of the tines, so, e.g., for acoustic waves generated by the light beam being absorbed by the cell walls. It also permits response times on the order of one second using a small sample volume, e.g., about 5 cc or about 2 cc but preferably less than about 1 cc.

This technique thus permits measurements which would be faster and more compact than present available techniques. Compared to conventional methods it requires much less sample volume and allows resonance with a higher Q thus making it possible to exclude more noise. The QEPAS technique is also less susceptible to spurious signals generated by absorption of the beam or scattered light by windows, cell walls, etc.

Figure 3:
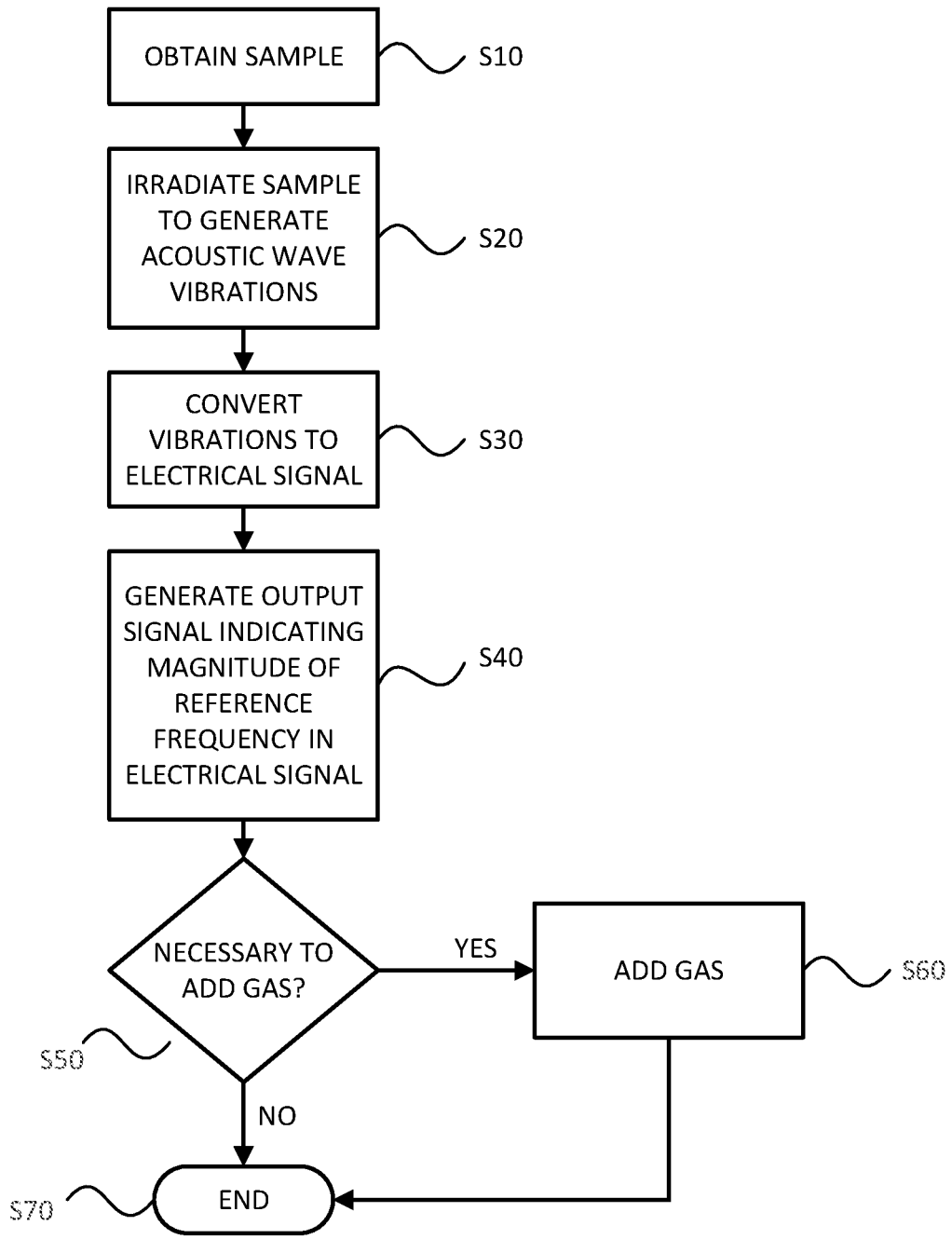
FIG. 3 is a flowchart illustrating the steps of an example of a process for replenishing gas in a laser chamber based on a measured number concentration of F2 in a laser gas.

FIG. 3 is a flowchart showing a method of replenishing gas in a laser chamber based on a measured number concentration of F2 in a laser gas. In a step S10 a sample of the gas in the laser chamber is obtained. In a step S20 at least a portion of the sample is irradiated with radiation modulated at a reference frequency to produce acoustic waves in the gas sample, the acoustic waves in turn inducing vibrations in a transducer located in the gas cell and having a resonant frequency substantially the same as the reference frequency. As mentioned, the sample may be irradiated with a laser or with an LED. In a step S30 the transducer converts the vibrations to an electrical signal by generating an electrical signal indicative of the vibrations. In a step S40 an output signal is generated which is indicative of a magnitude of a frequency component of the electrical signal at the reference frequency.

In a step S50 it is determined based on the output signal whether it is necessary to add gas containing fluorine to the gas in the laser chamber. If it is determined in step S50 that it is necessary to add gas then gas is added in a step S60 and then the process ends at a step S70. If it is determined in step S50 that it is not necessary to add gas then the process ends at a step S70.

The above description includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is construed when employed as a transitional word in a claim. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

What is claimed is:

1. Apparatus comprising:
 a laser chamber adapted to retain a laser gas containing fluorine;
 a gas cell in selective fluid communication with the laser chamber for retaining a sample of the laser gas;
 a frequency generator for producing a frequency signal having a reference frequency;
 a radiation source arranged to receive the frequency signal and to irradiate at least a portion of the gas sample with radiation modulated at the reference frequency to produce acoustic waves in the gas sample;

an acoustic resonator located in the gas cell and arranged to amplify the acoustic waves;

a piezoelectric quartz tuning fork located in the gas cell and having a resonant frequency substantially the same as the reference frequency and subjected to the acoustic waves in such a manner as to cause at least a portion of the piezoelectric quartz tuning fork to vibrate for generating an electrical signal indicative of a frequency at which the piezoelectric quartz tuning fork vibrates;

a preamplification circuit arranged to receive the electrical signal to produce an amplified electrical signal;

a lock-in amplifier arranged to receive the amplified electrical signal and for generating an output signal indicative of a magnitude of a frequency component of the electrical signal at the reference frequency;

a laser controller arranged to receive the electrical signal and adapted to determine based at least in part on the electrical signal a concentration of F2 in the sample gas and to generate an indication that it is necessary to add gas containing F2 to the laser chamber; and a gas supply system responsively connected to the laser controller and adapted to supply gas containing F2 to the laser chamber based at least in part on the indication from the laser controller.

* * * * *